US008471023B2

(12) United States Patent
Grote et al.

(10) Patent No.: US 8,471,023 B2
(45) Date of Patent: Jun. 25, 2013

(54) REDUCTIVE AMINATION OF 6-KETO NORMORPHINANS BY CATALYTIC HYDROGEN TRANSFER

(75) Inventors: Christopher W. Grote, Webster Groves, MO (US); Gary L. Cantrell, Troy, IL (US); Joseph P. McClurg, Manchester, MO (US); Catherine E. Thomasson, Webster Groves, MO (US); Frank W. Moser, Arnold, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 317 days.

(21) Appl. No.: 12/797,640

(22) Filed: Jun. 10, 2010

(65) Prior Publication Data

US 2010/0317861 A1 Dec. 16, 2010

Related U.S. Application Data

(60) Provisional application No. 61/186,047, filed on Jun. 11, 2009.

(51) Int. Cl.
*C07D 221/28* (2006.01)

(52) U.S. Cl.
USPC .......................................................... 546/74

(58) Field of Classification Search
None
See application file for complete search history.

(56) References Cited

U.S. PATENT DOCUMENTS

| 2,578,787 | A | 12/1951 | DeBenneville |
| 2,772,270 | A | 11/1956 | Weiss |
| 3,717,643 | A | 2/1973 | Archer |
| 4,089,855 | A | 5/1978 | Chatterjie et al. |
| 4,443,605 | A | 4/1984 | Kotick et al. |
| 4,521,601 | A | 6/1985 | Rice |
| 4,673,679 | A | 6/1987 | Aungst et al. |
| 4,775,759 | A | 10/1988 | Rice et al. |
| 4,795,813 | A | 1/1989 | Schwartz |
| 4,912,114 | A | 3/1990 | Revesz |
| 4,991,391 | A | 2/1991 | Kosinski |
| 5,240,933 | A | 8/1993 | Merz et al. |
| 5,336,483 | A | 8/1994 | de Costa et al. |
| 5,668,285 | A | 9/1997 | Rice et al. |
| 5,693,820 | A | 12/1997 | Helmchen et al. |
| 5,756,745 | A | 5/1998 | Kavka |
| 5,847,142 | A | 12/1998 | Mudryk et al. |
| 6,177,438 | B1* | 1/2001 | Nagase et al. ................. 514/280 |
| 6,184,381 | B1 | 2/2001 | Ikariya et al. |
| 6,323,212 | B1 | 11/2001 | Nagase et al. |
| 6,509,467 | B1 | 1/2003 | Blacker et al. |
| 6,887,999 | B1 | 5/2005 | Likhotvorik |
| 7,045,646 | B2 | 5/2006 | Tanis et al. |
| 7,230,134 | B2 | 6/2007 | Borner et al. |
| 2004/0267051 | A1 | 12/2004 | Boerner et al. |
| 2005/0038061 | A1* | 2/2005 | Schutz et al. ................. 514/282 |
| 2006/0182692 | A1 | 8/2006 | Fishburn et al. |
| 2008/0009629 | A1 | 1/2008 | Avdagic |
| 2008/0045715 | A1 | 2/2008 | Mitchell et al. |
| 2008/0234307 | A1 | 9/2008 | Schuetz et al. |
| 2010/0022774 | A1 | 1/2010 | Kvernenes et al. |
| 2010/0041888 | A1 | 2/2010 | Grote et al. |
| 2010/0081817 | A1* | 4/2010 | Hudson et al. ................. 546/44 |
| 2010/0216995 | A1* | 8/2010 | Grote et al. ................. 546/44 |
| 2010/0317683 | A1* | 12/2010 | Grote et al. ................. 514/282 |

FOREIGN PATENT DOCUMENTS

| CN | 1115318 | 1/1996 |
| CN | 1115318 A | 1/1996 |
| DE | 922 827 | 1/1955 |
| EP | 0 034 480 | 8/1981 |
| EP | 0 879 823 | 11/1998 |
| JP | 41-6905 | 4/1966 |
| JP | 41-7786 | 4/1966 |
| JP | 41-7787 | 4/1966 |
| WO | WO 2004/085058 | 10/2004 |
| WO | WO 2005/100361 | 10/2005 |
| WO | WO 2006/035195 | 4/2006 |
| WO | WO 2006/052710 | 5/2006 |
| WO | WO 2009/012005 A1 | 1/2009 |
| WO | WO 2010/144641 | 12/2010 |

OTHER PUBLICATIONS

Brossi, A., Atwell, L., Jacobson, A. E., Rozwadowska, M. D., Schmidhammer. 235. Structure-Activity Relationship of Oxygenated Morphinans. VII. 5-Methylated and 14-Hydroxy-substituted Agonists and Antagonists of the 4-Hydroxy- and 3,4-Dioxygenated 6-Morphinanone Series. Helvetica Chimica Acta. 1982, 65, 2394-2404.*
Vedejs, E. Substituted Isoquinolines by Noyori Transfer Hydrogenation: Enantioselective Synthesis of Chiral Diamines Containing an Aniline Subunit. Journal of Organic Chemistry. 1999, 64, 6724-6729.*
Abdel-Magid et al., "Reductive Animation of Aldehydes and Ketones . . . ", Tetrahedron Letters, vol. 31, No. 39, 1990, p. 5395-5598.
Beyerman et al., "Synthesis of racemic and optically active codeine and morphine via the N-formylnordihydrothebainones", Journal of the Royal Netherlands Chemical Society, 97, May 5, 1978, pp. 127-130.
Beyerman et al.,"Synthesis of racemic and of (+)- and (−)-1 methyldihydrothebainone. (Chemistry of opium alkaloids, Part IV)", Recl. Trav. Chim. Pays-Bas, 1976, 75, p. 184-188.
Bognar et al., Izvestiya po Khimiya, 1975, 81(1), p. 203-215.
Borch et al., "The cyanohydridoborate Anion as a Selective Reducing Agent", Journal of the American Chemical Society, 93:12, Jun. 16, 1971, p. 2897-2904.
Borch et al., "A New Method for the Methylation of Amines", J. Org. Chem., vol. 36, No. 10, 1972, pp. 1673-1674.
Brine et al., "Formamidinesulfinic Acid Reduction of Dihydrocodeinone Derivatives", J. Org. Chem., vol. 43, No. 8, 1978, p. 1555-1557.

(Continued)

*Primary Examiner* — Jason M Nolan
*Assistant Examiner* — Po-Chih Chen

(57) ABSTRACT

The present invention provides processes for the stereoselective synthesis of 6-alpha-amino morphinans. In particular, the invention provides processes for the reductive amination of 6-keto normorphinans by catalytic transfer hydrogenation.

17 Claims, No Drawings

OTHER PUBLICATIONS

Burke et al., "Probes for narcotic Receptor Mediated Phenomena . . .", Heterocycles, vol. 23, No. 1, 1985, p. 99-110.

Butora et al., "Chemoenzymatic Synthesis of the Morphine Skeleton via Radical . . .", Tetrahedron Letters, vol. 37, No. 45, 1996, p. 8155-8158.

Campbell et al., "The Preparation of Unsymmetrical Secondary Aliphatic Amines", Jan. 1944, vol. 66, p. 82-84.

Chatterjie et al., "Reduction of 6-Ketones of the Morphine Series . . .", J. Org. Chem., vol. 41, No. 22, 1976, p. 3624-3625.

De Benneville et al., "The Behavior of aliphatic Aldehydes in the Leuckart-Wallach Reaction", J. Am. Chem. Soc., 1950, 72, pp. 3073-3075.

De Costa et al., "Probes for Narcotic Receptor Mediated Phenomena . . .", J. Med. Chem., 35, p. 2826-2835, 1992.

Farber et al., "A Synthesis of Armepavine and Related Bases. Resolution of (±)-Armepavine", Anales. Asoc. Quim. Argentina, 58, 1970, pp. 133-138.

Farber et al., "Resolution of (±)-armepavine", Chemistry and Industry, Jan. 13, 1968, pp. 57-58.

Fujii et al., "The First Example of the Stereoselective Synthesis of . . .", Chem. Pharm. Bull., 52(6), 2004, p. 747-750.

Fujii et al., "Ruthenium(II)-Caatalyzed Asymmetric Transfer . . .", J. Am. Chem. Soc., 1996, 118, p. 2521-2522.

Gao et al., "Synthesis of 7-Arylmorphinans . . .", J. Med. Chem., 1998, 41, p. 3901-3098.

Gorlitzer et al., "Diepoxy-bis-(iminoethano)-dinaphth[2,1-b:1',2'-i]acridine$^{2,3+}$", Arch. Pharm. (Weinheim) 325, 1992, p. 637-641.

Greene et al., "Protection for Phenols", Protective Groups in Organic Synthesis, 3$^{rd}$, Ed., c1999, pp. 249-257 and 266-269.

Gribble et al., "Reactions of Sodium Borohydride in Acidic Media . . .", Communications, Aug. 1987, p. 709-711.

Hashiguchi et al., "Asymmetric Transfer Hydrogenation of Aromatic ketones Catalyzed by chiral Ruthenium(II) Complexes", J. Am. Chem. Soc., vol. 177, No. 28, 1995, p. 7562-7563.

Huang et al., "Synthesis of (+−)-Glaucine and (+−)-Neospirodienone via an One-Pot Bischler-Napieralski Reaction and Oxidative Coupling by a Hypervalent Iodine Reagent", Helvetica chimica Acta 2004 CH, vol. 887, No. 1, 2004, pp. 167-174, XP002476119.

Kalimin et al., "Palladium-Catalyzed 2-Phenylethenylation of Codeine . . .", Helevetica Chimca Acta, vol. 89, 2006, p. 861-869.

Kametani et al., "131. Coclaurine 7-Benzyloxy-1,2,3,4-tetrahydro-1-(p-hydroxyphenyl)-6-methoxy-2-methylisoquinoline 7-Benzyloxy-1,2,3,4-tetrahydro-1-(p-hydroxybenzyl)-6-methoxy-2-methylisoquinoline", Coclaurine, vol. 87, No. 7, 1967, pp. 757-760.

Kametani et al., "131. Coclaurine 7-Benzyloxy-1,2,3,4-tetrahydro-1-(p-hydroxyphenyl)-6-methoxy-2-methylisoquinoline", Coclaurine, vol. 87, No. 7, 1967, pp. 757-760, English Translation.

Kashdan et al., "Synthesis of 1,2,3,4-Tetrahydroisoquinolines", J. Org. Chem., 1982, 47, pp. 2638-2643.

Kirby et al., "Synthesis of 14B-Mercaptocodeine Derivatives from N-t-Butoxycarbonyl-N-northebaine", Journal of chemical Research, Miniprint., 1984, pp. 2073-2086, XP9127313.

Kitamura et al., "General Asymmetric Synthesis of Isoquinoline Alkaloids. Enantioselective Hydrogenation of Enamides Catalyzed by BINAP-Ruthenium(II) Complexes", J. Org. Chem., 1994, 59, pp. 297-310.

Klunenberg et al., "A Remarkable Influence of the Electrolyte in Andoic cyclization of 1-Benzyltetrahydroisoquinolines to neospirodienones or Morphinandienones", Tetrahedron Letters, 1982, vol. 23, No. 44, pp. 4581-4584.

Koolpe et al., "Opioid Agonists and Antagonists. 6-Desoxy-6-substituted . . .", J. Med. Chem., 1985, 28(7), p. 949-957.

Lau et al., "Evolution of a Series of Non-Quinoline Leukotriene D$_4$ Receptor Antagonist . . .", Bioorganic & Medicinal chemistry Letters, vol. 5, No. 15, 1995, p. 1615-1620.

Lazar et al., "A Selective Removal of Benzyl Protecting Groups in Arylphosphate Esters with Bromotrimethylsilane", Synthetic Communications, 22(6), 1992, p. 923-931.

Leland et al., "Analgesic narcotic antagonists. 5. 7,7-Dimethyldihydrocodeines . . .", J. Med. Chem., 1981, 24, p. 717-721.

Lespagnol et al., "Préparation d'amides de l'homovératrylamine et d'acids iodophénylacétiques substitutés", Chim. Therap., 1965, pp. 14-16.

Lespagnol et al., "Preparation of amides from the homoveratrylamine and iodephenylacetic substituted acids", Chim. Therap., 1965, pp. 14-16, English Translation by FAST-TRANS.

Malspeis et al., "Metabolic Reduction of Naltrexone I. Synthesis, Separation . . .", Res. Commun. Chem. Pathol. Pharmacol, 2(43), 1975.

Mao et al., "A Chiral Rhodium Complex for Rapid Asymmetric Transfer . . .", Organic Letters, 1999, vol. 1, No. 6, p. 841-843.

Meuzelaar et al., "Chemistry of Opium Alkaloids, 45 Improvements in the Total Synthesis of Morphine", Eur. J. Org. Chem., 1999, pp. 2315-2321.

Mohamed et al., "Stereoselectivity of the Reduction of Naltrexone Oxime with Borane", Journal of Organic chemistry, 1986, 51(1), pp. 105-106.

Nagase et al., "The Facility of Formation of a $\Delta^6$ Bond in Dihydromorphinone and Related Opiates", J. Org. Chem., 1989, 54, p. 4120-4125.

Nagata et al., "Synthetic Studies on Isoquinoline Alkaloids, I, An Efficient Synthesis of 9,10-Substituted Protoberberine Alkaloids", Chem. Pharm. Bull., 194, 23(11), pp. 2867-2877, 1975.

Noyori et al., "Asymmetric Catalysts by Architechtural and Functional Molecular . . .", Agew. Chem. Int., Ed. 2001, 40, p. 40-73.

Noyori et al., "Asymmetric Transfer Hydrogenation Catalyzed by Chiral Ruthenium Complexes", Acc. Chem. Res., 1997, 30, pp. 97-102.

Ohno et al., "Solid-Phase synthesis of 6-Silfionylamino Morphinan Libraries", Synlett, 2002, No. 1, p. 93-96.

Olfoson et al., "A New Reagent for the Selective, High-Yield N-Dealkylation of Teritary Amines: Improved Syntheses of Naltrexone and Nalbuphine", J. Org. Chem.., 1984, 49, p. 2081-2082.

Olieman et al., "Conversion of (−)-dihydrocodeinone into....", Laboratory of Organic chemistry Technische Hogeschool Delft, Julianalaan 136, Delft, The Netherlands, Mar. 15, 1976.

Olsen et al., "Conjugate Addition Ligands of Opioid Antagonists . . .", J. Med. Chem., 1990, 33(2), p. 737-741.

Palmer et al., "Asymmetric transfer hydrogenation of C═O and C═N bonds", Tetrahedron: Asymmetry 10, 1999, p. 2045-2061, XP 004174087.

Puntener et al., "New Efficient Catalysts for enantioselective Transfer Hydrogenations", Tet. Lett., 1996, 37(45), p. 8165-8168.

Sagara et al., "Specific Affinity Labeling of....", Bioorganic & Medicinal Chemistry Letters, vol. 5, No. 15, 1995, p. 1609-1614.

Saunders et al., "Assessment of relative nutritive value of proteins using streptoccus zymogenes", Chemistry and Industry, Jan. 13, 1968, pp. 56-58.

Sayre et al., "Stereospecific synthesis of the 6a- and 6b-Amino Derivatives of Naltrexone and Oxymorphone", J. Org. Chem., 1980, 45, pp. 3366-3368.

Schellenberg, "The Synthesis of Secondary and Tertiary Amines by Borohydride Reduction", Nov. 1963, p. 3259-3261.

Schmidhammer, "134, Synthesis and Biological ion of 14-Alkoxymorphinans Part 4) Opioid Agonists and Partial Opioid Agonists in a Series of . . .", Helevitca Chimca Acta, vol. 72, 1989, p. 1233-1239.

Schütz et al., "Synthesis of 6-amino Acid Substituted Derivatives of the Highly Potent Analgesic 14-O-methyloxymorphone", Helvetica Chimica Acta, 2003, 86(6), pp. 2142-2148.

Seki, "Studies on the Morphine Alkaloids . . .", vol. 84, No. 7, p. 626-631, Jul. 1964.

Seki, "Studies on the Morphine Alkaloids . . .", vol. 84, No. 7, p. 626-631, English Translation, Jul. 1964.

Sheth et al., "Synthesis of N-(3',4'-Dimethoxy-5'-bromophenethyl)-2-(4''-hydrioxyphenyl)-acetamide & Allied Products", Indian Journal of Chemistry, vol. 15B, Jul. 1977, pp. 595-598.

Simon et al., "Stereoselective Synthesis of β-naltrexol, β-naloxol, β-naloxamine, β-naltrexamine and Related Compounds by the Application of the Mitsunobu Reaction", Tetrahedron, 1994, 50(32), pp. 9757-9768.

Small et al., "The Addition of Organomagnesium Halides to Pseudocodeine Types. IV. Nuclear-Substituted Morphine Derivatives", Contribution from the Cobb Chemical Laboratory, University of Virginia, pp. 204-232.

Spadoni et al., "2-[N-Acylamino($C_1$-$C_3$)alkyl]indoles as $MT_1$ . . .", J. Med. Chem., 1998, 41, p. 3624-3634.

Tolkachev et al., "Synthetic Investigation in [Kurarealkaloidov] Area XVI. Synthesis 1-(e'-Bromine....", Organicheskoi Khimii, 1966, 36(10), pp. 1767-1772.

Tolkachev et al., "Synthetic Investigation in [Kurarealkaloidov], Area XVI. Synthesis 1-(e'-Bromine....", Organicheskoi Khimii, 1966, 36(10), pp. 1767-1772, English Translation provided by FAST-TRANS.

Uba et al., "Stereospecific Synthesis of Codeine . . .", Chem. Pharm. Bull., vol. 27, Issue 9, 1979, p. 2257-2258.

Uematsu et al., "Asymmetric Transfer Hydrogenation of Imines", J. Am. Chem. Soc., 1996, 118, p. 4916-4917.

Uwai et al., "Syntheses and receptor-binding studies of derivatives . . .", Bioorganic & Medicinal Chemistry, 12, 2004, p. 417-421, XP 002488979.

H.C. van der Plas et al., "On the reaction of 2-, 3- and 4-bromo(chloro)-1,8-naphthridine with potassium amide in liquid ammonia", Laboratory of Organic Chemistry, Agricultural University, Wagenagen, The Netherlands, 1978.

Van Gurp et al., "Synthesis of 7,8-Didehydro-3,4-Dimethoxy . . .", Bull, Soc. Chim. Belg., vol. 96/n° Apr. 1987, p. 325-329, 1987.

Venkov et al., "Synthesis of isoquinolines from 2-phenylethylamines, amides, nitriles and carboxylic acids in polyphosphoric acid",Tetrahedron 19960909 GB, vol. 52, No. 37, Sep. 9, 1996, pp. 12299-12308, XP 002476120.

Voronin et al., "Synthetic Investigations in the Field of the Curare Alkaloids XII. Synthesis of Isomeric Tubocurarin Iodides", Chemistry of heterocyclic Compounds, Chemistry of Heterocyclic Compounds, 1967, pp. 447-450 (English Translation of Voronin et al., Khimiya Geterotsiklicheskikh Soedinenii, 1969, 4, pp. 606-610).

Watanabe et al., "Novel Synthesis of the Ortho Ester Derivative of the 4,5-Epoxymorphinan", Organic Letters, vol. 8, No. 3, 2006, p. 523-526.

White et al., "Asymmetric Total Synthesis of (+)-Codeine via . . .", J. Org. Chem., 1999, 64, p. 7871-7884.

White et al., "Asymmetric Synthesis of (+)-Morphine . . .", J. Org. Chem., 1997, 62, p. 5250-5251.

Wu et al., "Asymmetric transfer hydrogenation of imines and iminiums....", Chem. Commun., 2006, p. 1766-1768.

Yamakawa et al., "The Methal-Ligand Bifunctional Catalysis: A Theoretical Study on . . .", J. Am. Chem. Soc., 2000, 122, p. 1466-1478.

Takemori et al., "Stereochemical Studies on Medicinal Agents....", Journal of Medicinal Chemistry, 1977, 20(8), pp. 1100-1102.

Reddy et al., "A convenient method for the N-formylation of secondary amines . . .", JTetrahedron Letters, 41, 2000, pp. 9149-9151.

* cited by examiner

REDUCTIVE AMINATION OF 6-KETO NORMORPHINANS BY CATALYTIC HYDROGEN TRANSFER

CROSS REFERENCE TO RELATED APPLICATIONS

This application claims the benefit of U.S. Provisional Application No. 61/186,047 filed Jun. 11, 2009, which is incorporated herein in its entirety.

FIELD OF THE INVENTION

The present invention generally relates to the reductive amination of 6-keto normorphinans to form 6-alpha-amino epimers. In particular, the invention relates to the reductive amination of 6-keto normorphinans by catalytic hydrogen transfer to form N-formylated 6-alpha-amino epimers.

BACKGROUND OF THE INVENTION

Morphinans, including N-alkylated morphinans and normorphinans, are important pharmaceuticals, typically used as analgesics or drug/alcohol cessation agents. Substituted morphinans, such as 6-amino derivatives, may be useful therapeutically because they have higher efficacy, greater potency, and/or may function as prodrugs. Although several methods for forming 6-amino morphinans from 6-keto morphinans have been reported in the literature, none provides the stereoselective synthesis of 6-alpha-amino epimers in good yield. Furthermore, the existing methods require the use of highly reactive reducing agents and/or hydrogen gas. There is a need, therefore, for simple, mild, and efficient processes for the preparation of 6-alpha-amino morphinans of high enantiomeric purity.

SUMMARY OF THE INVENTION

The present invention provides processes for the stereoselective synthesis of 6-alpha-amino epimers by the reductive amination 6-keto normorphinans in a hydrogen transfer donor environment.

Briefly, therefore, one aspect of the present invention encompasses a process for preparing a 6-alpha-amino-N17-formyl morphinan. The process comprises contacting a 6-keto normorphinan with an amine source, a hydrogen donor comprising a formate ion, a transition metal catalyst, and a proton acceptor to form the 6-alpha-amino-N17-formyl morphinan.

Another aspect of the invention provides a process for preparing a compound comprising Formula (IV):

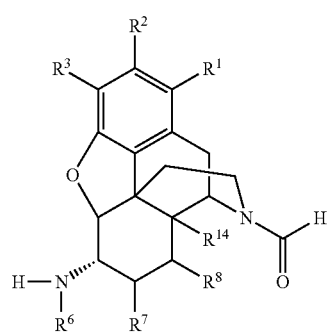

The process comprises reducing a compound comprising Formula (I) in the presence of an amine source ($R^6NH_2$), a hydrogen donor comprising a formate ion, a transition metal catalyst, and a proton acceptor to form the compound comprising Formula (IV). The compound of Formula (I) comprises:

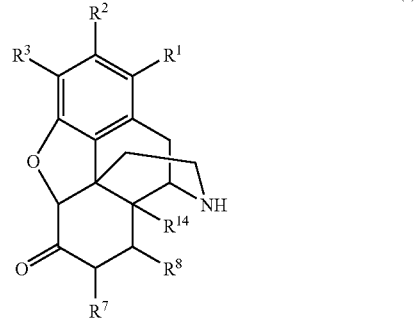

For each of the compounds comprising Formulas (I) or (IV), the variables stand for the following:
 $R^1$ and $R^2$ are independently selected from the group consisting of hydrogen, hydrocarbyl, substituted hydrocarbyl, halogen, and $\{-\}OR^{15}$;
 $R^3$, $R^7$, and $R^8$ are independently selected from the group consisting of hydrogen, hydrocarbyl, substituted hydrocarbyl, and $\{-\}OR^{15}$;
 $R^6$ is selected from the group consisting of hydrogen, hydrocarbyl and substituted hydrocarbyl;
 $R^{14}$ is selected from the group consisting of hydrogen and $\{-\}OR^{15}$; and
 $R^{15}$ is selected from the group consisting of hydrogen, hydrocarbyl, substituted hydrocarbyl, and a hydroxy protecting group.

A further aspect of the invention encompasses a composition comprising a compound of Formula (IV) and less than about 5% of a 6-beta amino epimer of the compound comprising Formula (IV):

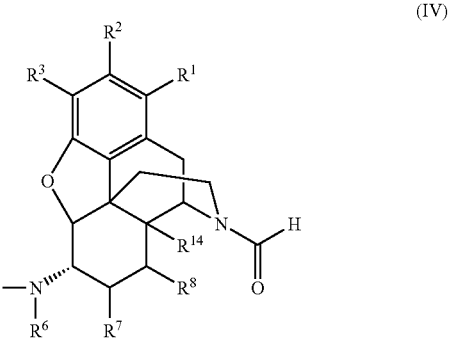

wherein:
 $R^1$ and $R^2$ are independently selected from the group consisting of hydrogen, hydrocarbyl, substituted hydrocarbyl, halogen, and $\{-\}OR^{15}$;
 $R^3$, $R^7$, and $R^8$ are independently selected from the group consisting of hydrogen, hydrocarbyl, substituted hydrocarbyl, and $\{-\}OR^{15}$;
 $R^6$ is selected from the group consisting of hydrogen, hydrocarbyl and substituted hydrocarbyl;

$R^{14}$ is selected from the group consisting of hydrogen and {—}$OR^{15}$; and $R^{15}$ is selected from the group consisting of hydrogen, hydrocarbyl, substituted hydrocarbyl, and a hydroxy protecting group.

Other features and iterations of the invention are described in more detail below.

DETAILED DESCRIPTION OF THE INVENTION

The present invention provides improved processes for the stereoselective synthesis of 6-alpha-amino morphinan epimers, salts, intermediates, or analogs thereof. In particular, the 6-keto moiety of a normorphinan is converted to the 6-alpha-amino epimer by reductive amination in a transfer hydrogenation environment. Specifically, the 6-keto moiety of the normorphinan is condensed with an amine source in the presence of a transition metal catalyst and a hydrogen donor comprising a formate ion, such that a 6-alpha-amino-N17-formyl morphinan is formed. The processes of the invention, therefore, avoid the use of hydrogen gas and highly reactive main group reducing agents. Accordingly, the processes are quite mild and tolerate many functional groups that may be reduced in the presence of less hazardous main group reducing agents. Advantageously, the processes of the invention provide high yield and high epimeric purity of 6-alpha-amino epimers. The present invention also provides compositions comprising a 6-alpha-amino-N17-formyl morphinan epimer and less than 5%, preferably less than 2%, and even more preferably less than 1% of a 6-beta amino epimer.

(I) Processes for the Preparation of 6-Alpha-Amino-N17-Formyl Morphinans

One aspect of the invention encompasses processes for the stereoselective synthesis of 6-alpha-amino-N17-formyl morphinans. The processes comprise contacting a 6-keto normorphinan with an amine source such as a primary amine or an ammonium salt, a hydrogen donor comprising a formate ion, a transition metal catalyst, and a proton acceptor to form the 6-alpha-amino-N17-formyl morphinan.

In general, the morphinans detailed herein comprise any compound having a core morphinan structure. For the purposes of illustration, the ring atoms of the core morphinan structure are numbered in the diagram presented below. Normorphinans lack a substituent on the nitrogen at position 17. That is, at least one hydrogen atom is linked to the nitrogen of the ring.

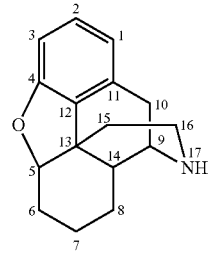 [SMILES: c1cc2c3c(c1)OC1CCCC4C(C2)NCCC314]

Contact of the 6-keto normorphinan with the amine source, the transition metal catalyst, and the hydrogen donor leads to formation of two intermediate compounds, i.e., a bis-formate salt of 6-imine normorphinan and a formate salt of 6-imine-N17-formyl morphinan. The imine moiety of each intermediate is converted in situ to the 6-alpha-amino epimer. Extension of the reaction drives the formation of the 6-alpha-amino-N17-formyl species. Contact of the formate salt of the 6-alpha-amino-N17-formyl morphinan with the proton acceptor yields the 6-alpha-amino-N17-formyl morphinan.

(II) Processes for the Preparation of Compounds Comprising Formula (IV)

In one embodiment of the invention, a compound comprising Formula (IV) is prepared from a compound comprising Formula (I). The process comprises reducing the compound comprising Formula (I) in the presence of an amine source ($R^6NH_2$), a hydrogen donor comprising a formate ion, and a transition metal catalyst, wherein two intermediate compounds comprising Formulas (IIa) or (IIb) are formed. The compounds comprising Formulas (IIa) or (IIb) are converted in situ to a compound comprising Formula (III). The process further comprises contacting the compound comprising Formula (III) with a proton acceptor to form the compound comprising Formula (IV). For purposes of illustration, Reaction Scheme 1 depicts the synthesis of the compound comprising Formula (IV) in accordance with one aspect of the invention:

Reaction Scheme 1:

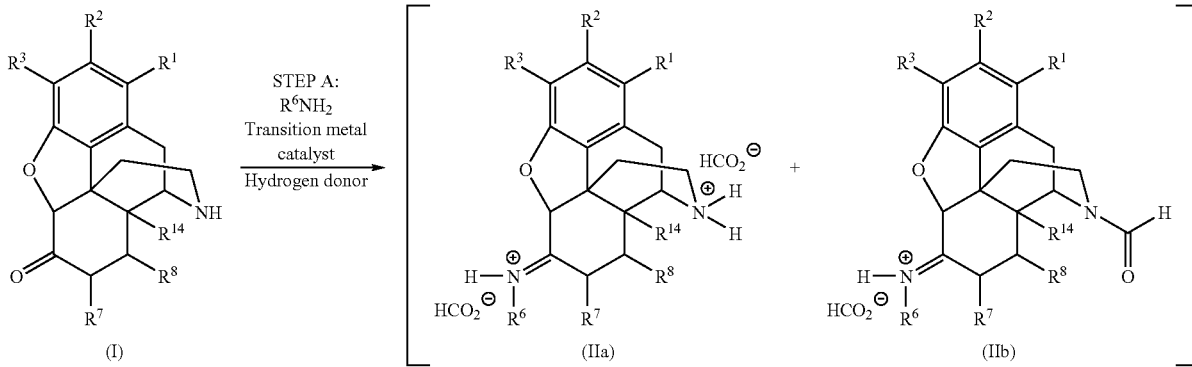

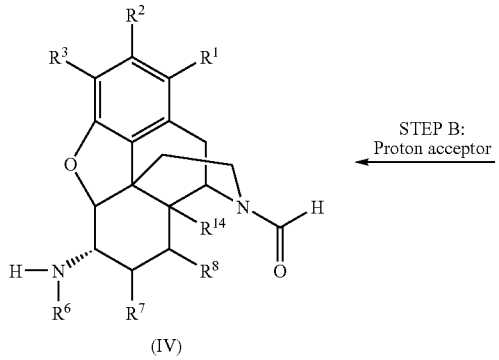

(IV)

STEP B: Proton acceptor

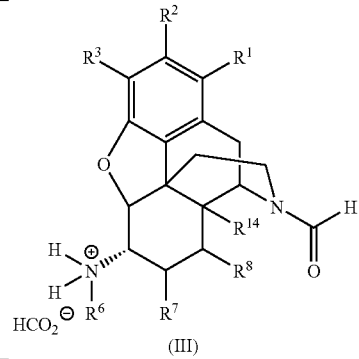

(III)

wherein:

R¹ and R² are independently selected from the group consisting of hydrogen, hydrocarbyl, substituted hydrocarbyl, halogen, and {—}OR$^{15}$;

R³, R⁷, and R⁸ are independently selected from the group consisting of hydrogen, hydrocarbyl, substituted hydrocarbyl, and {—}OR$^{15}$;

R⁶ is selected from the group consisting of hydrogen, hydrocarbyl and substituted hydrocarbyl;

R$^{14}$ is selected from the group consisting of hydrogen and {—}OR$^{15}$; and R$^{15}$ is selected from the group consisting of hydrogen, hydrocarbyl, substituted hydrocarbyl, and a hydroxy protecting group.

In one preferred embodiment, each of R¹, R², R⁷, and R⁸ are hydrogen. In another preferred embodiment, R$^{14}$ is hydrogen or hydroxy. In yet another preferred embodiment, R³ is selected from the group consisting of alkoxy, hydroxy, and protected hydroxy.

(a) Step A of the Process

The process commences with the formation of a reaction mixture by combining a 6-keto normorphinan comprising Formula (I) with an amine source, a hydrogen donor comprising a formate ion, and a transition metal catalyst, wherein the compound comprising Formula (I) undergoes reductive amination. A variety of compounds comprising Formula (I) are suitable for use in the process. In exemplary embodiments, R¹, R², R⁷, and R⁸ are each hydrogen; R³ is hydroxy or methoxy; and R$^{14}$ is hydrogen or hydroxy. Representative compounds comprising Formula (I) include, but are not limited to, norhydrocodone, norhydromorphone, noroxycodone, and noroxymorphone, which are depicted below:

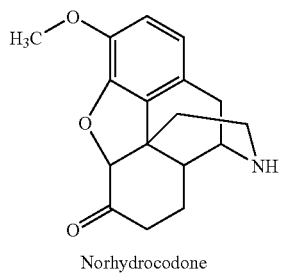

Norhydrocodone

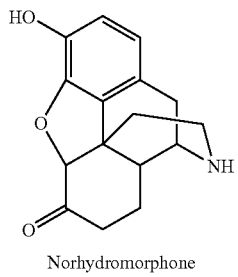

Norhydromorphone

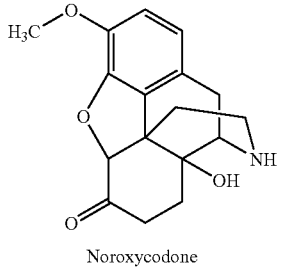

Noroxycodone

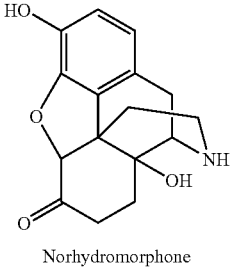

Norhydromorphone (i) Amine Source

The reaction mixture also comprises an amine source comprising formula R⁶NH₂, wherein R⁶ is selected from the group consisting of hydrogen, hydrocarbyl, and substituted hydrocarbyl. In embodiments in which R⁶ is hydrogen, the amine source, ammonia (NH₃), is provided by an ammonium salt. The ammonium salt may comprise an inorganic anion or an organic anion. Non-limiting examples of suitable inorganic anions include bicarbonate, carbonate, chloride, hydroxide, nitrate, phosphate, sulfide, and sulfate. Examples of suitable organic anions include, but are not limited to, benzoate, butanoate, acetate, citrate, formate, fumarate, glutamate, lactate, malate, propionate, oxalate, succinate, and tartarate. In a preferred embodiment, the ammonium salt is ammonium acetate.

In embodiments in which R⁶ is hydrocarbyl or substituted hydrocarbyl, the amine source is a primary amine. In preferred embodiments, R⁶ is alkyl, substituted alkyl, alkenyl, substituted alkenyl, alkynyl, substituted alkynyl, aryl, heteroaryl, carbocyclic, or heterocyclic. Non-limiting examples of suitable primary amines include methylamine, ethylamine, isopropylamine, allylamine, n-benzylamine, aniline (i.e., phenylamine), methanolamine, ethanolamine, and amino acids such as alanine or the methyl ester of alanine.

The molar ratio of the compound comprising Formula (I) to the amine source can and will vary depending on whether the amine source is an ammonium salt or a primary amine. In embodiments in which the amine source in an ammonium salt, the molar ratio of the compound comprising Formula (I) to the ammonium salt typically will range from about 1:2 to about 1:20. In some embodiments in which the amine source in an ammonium salt, the molar ratio of the compound comprising Formula (I) to the ammonium salt may range about 1:2 to about 1:5, from about 1:5 to about 1:10, from about 1:10 to about or 1:15, or from about 1:15 to about 1:20. In a preferred embodiment in which the amine source in an ammonium salt, the molar ratio of the compound comprising Formula (I) to the ammonium salt may range from about 1:11 to about 1:13, or more preferably about 1:12. In embodiments in which the amine source is a primary amine, the molar ratio of the compound comprising Formula (I) to the primary amine typically will range from about 1:1 to about 1:5. In various embodiments in which the amine source is a primary amine, the molar ratio of the compound comprising Formula (I) to the primary amine may be range from about 1:1 to about 1:2, from about 1:2 to about 1:3, or from about 1:3 to about 1:5. In a preferred embodiment in which the amine source is a primary amine, the molar ratio of the compound comprising Formula (I) to the primary amine may be range from about 1:1.25 to about 1:2.

(ii) Hydrogen Donor Comprising a Formate Ion

In addition to the compound comprising Formula (I) and the amine source, the reaction mixture also comprises a hydrogen donor comprising a formate ion, such that a transfer hydrogenation reaction may occur. Non-limiting example of suitable hydrogen donors comprising a formate ion include formic acid, an inorganic salt of formic acid, an organic salt of formic acid, or a mixture of formic acid and an organic base. Suitable inorganic salts of formic acid include, but are not limited to, calcium formate, cesium formate, lithium formate, magnesium formate, potassium formate, and sodium formate. Non-limiting examples are suitable organic salts of formic acid include ammonium formate, ethyl formate, methyl formate, amine formate, butyl formate, propyl formate, triethyl orthoformate, triethyl orthoformate, triethylammonium formate, trimethylammonium formate, and the like. Suitable organic bases for combining with formic acid include, but are not limited to, pyridine, triethylamine, diisopropylethylamine, N-methylmorpholine, and N,N-dimethylaminopyridine. In an exemplary embodiment, the hydrogen donor comprises a mixture of formic acid and an organic base, wherein the organic base is triethylamine.

The molar ratio of the compound comprising Formula (I) to the hydrogen donor can and will vary. In general, the molar ratio of the compound comprising Formula (I) to the hydrogen donor will range from about 1:1 to about 1:20. In various embodiments, the molar ratio of the compound comprising Formula (I) to the hydrogen donor may range from 1:1 to about 1:3, from about 1:3 to about 1:10, or from about 1:10 to about 1:20. In preferred embodiments, the molar ratio of the compound comprising Formula (I) to the hydrogen donor may range from 1:11 to about 1:13. In exemplary embodiments in which the hydrogen donor comprises formic acid and triethylamine, the molar ratio of the compound comprising Formula (I) to triethylamine may range from about 1:1 to about 1:10, or more preferably from about 1:3 to about 1:5. The hydrogen donor may be slowly introduced into the reaction mixture. For example, the hydrogen donor may be added in small aliquots or drops to the reaction mixture.

(iii) Transition Metal Catalyst

The reaction mixture also comprises a transition metal catalyst. As used herein, the transition metal catalyst comprises at least one metal complexed with at least one ligand. The metal of the catalytic transition metal complex may be ruthenium, osmium, rhodium, iridium, palladium, or platinum. In a preferred embodiment, the transition metal may be ruthenium, iridium, or rhodium. The valence state of the transition metal may vary. For example, non-limiting examples of suitable transition metals include ruthenium(II), ruthenium(III), ruthenium(IV), osmium(II), osmium(III), osmium(IV), rhodium(I), rhodium(III), iridium(III), iridium(IV), palladium(II), palladium(IV), platinum(II), and platinum(IV). Typically, the ratio of metal to ligand in the complex is about 1:1. The ligand of the catalytic transition metal complex may be a mono- or bidentate nitrogen donor, a phosphorous donor ligand, a cyclopentadienyl ligand, an arene ligand, an olefin ligand, an alkyne ligand, a heterocycloalkyl ligand, a heteroaryl ligand, a hydride ligand, an alkyl ligand, or a carbonyl ligand.

In preferred embodiments, the catalytic transition metal complex may be dichloro(arene)Ru(II) dimer, dichloro(pentamethylcyclopentadienyl)Rh(II) dimer, BINAP-Ru(II) diacetate, BINAP-Ru(II) dichloride, BINAP-Ru(II) dibromide, BINAP-Ru(II) diiodide, [RuCl((R or S)BINAP)($C_6H_6$)]Cl, dichloro(pentamethylcyclopentadienyl)iridium(III) dimer, Ru(III) chloride, $RuCl_3$ hydrate, Ru(III) acetylacetonate, tetraalkylammonium $RuCl_4$, or pyridinium $RuCl_4$. In an exemplary embodiment, the transition metal catalyst may be dichloro(p-cymene)Ru(III) dimer.

In other embodiments, the catalytic transition metal complex may be an asymmetric catalyst in which at least one metal is complexed with at least one bidentate, chiral ligand using nitrogen, oxygen, or phosphorous donor atoms. These catalysts are sometimes referred to as Noyori catalysts, and are more fully described in, for example, U.S. Pat. No. 5,693,820 (Helmchen et al.) and R. Noyori et al., *Asymmetric Catalysts by Architechtural and Functional Molecular Engineering: Practical Chemo- and Stereoselective Hydrogenation of Ketones*, Agew. Chem. Int. Ed. 2001, 40, pp. 40-73. In one example, the chiral ligand may comprise Formula (670), (680), (690), or (700), as shown below,

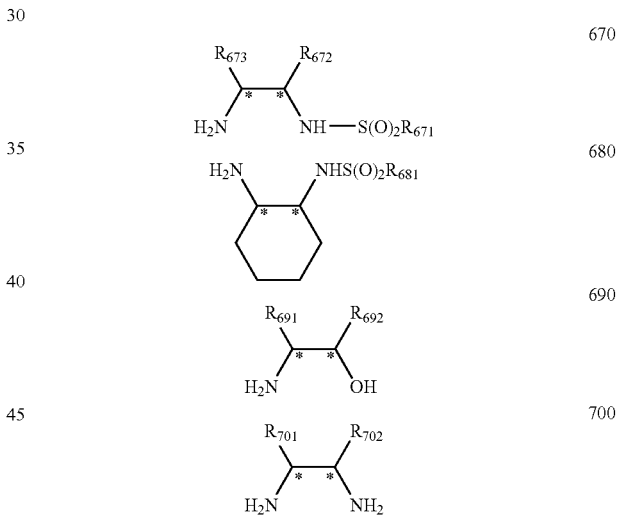

wherein $R_{671}$, $R_{672}$, $R_{673}$, $R_{681}$, $R_{691}$, $R_{692}$, $R_{701}$, and $R_{702}$ are independently alkyl or aryl and wherein $R_{691}$ and $R_{692}$ of Formula (690) and $R_{701}$ and $R_{702}$ of Formula (700), and the carbon atoms to which they are attached, may optionally form a cyclic or bicyclic compound. In the above structures, the "*" indicates a chiral carbon atom. The configuration of the chiral carbons of the asymmetric catalyst may be RR, RS, SR, or SS.

In one embodiment, the ligand comprises Formula (670) and $R_{672}$ and $R_{673}$ are each phenyl and $R_{671}$ is aryl. In another example of this embodiment, $R_{671}$ is tolyl, mesityl, or naphthyl. In an alternative embodiment, the ligand comprises Formula (680) and $R_{681}$ is tolyl, mesityl, 2,4,6-triisopropylphenyl, or naphthyl. In another example, the ligand comprises Formula (690) and $R_{691}$ and $R_{692}$ are hydrogen thus forming the compound, aminoethanol. In an alternative example, the ligand comprises Formula (690) and $R_{691}$ and $R_{692}$ are selected to form the following compound:

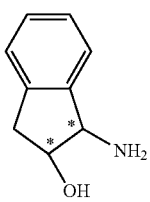 [SMILES: NC1c2ccccc2CC1O]

In another embodiment, the ligand corresponds to Formula (700) and $R_{701}$ and $R_{702}$ are hydrogen thus forming the compound, ethylenediamine.

In a preferred example, the chiral ligand may be p-toluenesulfonyl-1,2-diphenylethylenediamine, (1S,2S)-(+)-N-4-toluenesulfonyl-1,2-diphenylethylene-1,2-diamine, (1R,2R)-(−)-N-4-toluenesulfonyl-1,2-diphenylethylene-1,2-diamine, dl-N-tosyl-1,2-diphenylethylenediamine, N-tosyl-1,2-diphenylethylenediamine, N-tosyl-1,2-ethylenediamine, or N-tosyl-1,2-diaminocyclohexane.

Suitable ruthenium or rhodium asymmetric catalysts include the following:

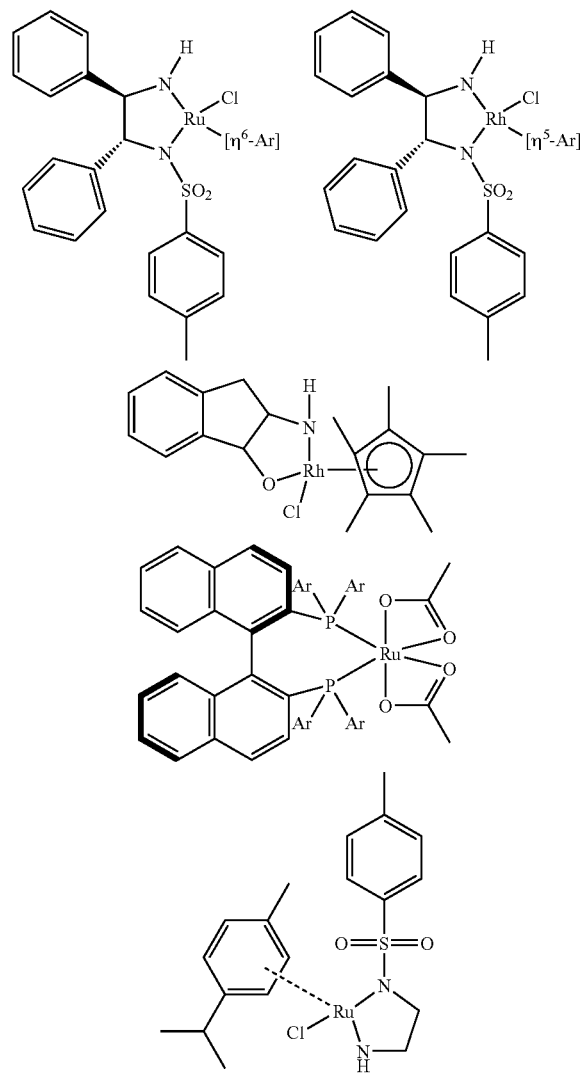

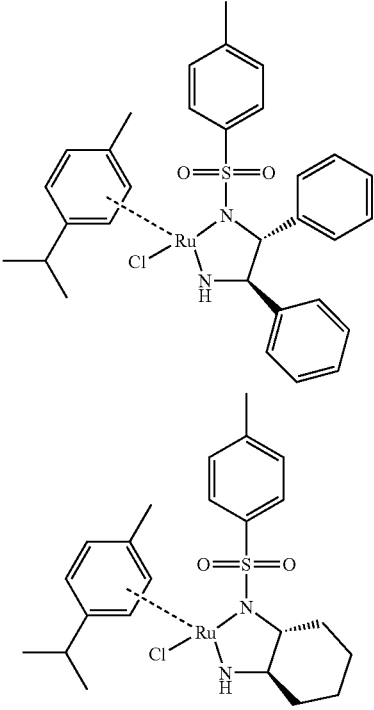

The molar ratio of the compound comprising Formula (I) and the transition metal catalyst can and will vary depending, for example, on the nature of the transition metal catalyst. In general, the molar ratio of the compound comprising Formula (I) and the transition metal catalyst will range from about 1:0.0001 to about 1:0.01. In some embodiments, the molar ratio of the compound comprising Formula (I) and the transition metal catalyst may range from about 1:0.0001 to about 1:0.001, or more preferably from about 1:0.001 to about 1:0.01.

(iv) Solvent

The reaction mixture, as detailed herein, also comprises a solvent. The solvent can and will vary depending on the starting substrate and the reactants used in the process. The solvent may be a protic solvent, an aprotic solvent, a non-polar solvent, or combinations thereof. Suitable examples of protic solvents include, but are not limited to, methanol, ethanol, isopropanol, n-propanol, isobutanol, n-butanol, s-butanol, t-butanol, water, and combinations thereof. Non-limiting examples of suitable aprotic solvents include acetonitrile, diethoxymethane, N,N-dimethylacetamide (DMAC), N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, 1,4-dioxane, N-methyl-2-pyrrolidinone (NMP), ethyl formate, formamide, hexamethylphosphoramide, N-methylacetamide, N-methylformamide, methylene chloride, nitrobenzene, nitromethane, propionitrile, sulfolane, tetramethylurea, tetrahydrofuran (THF), 2-methyl tetrahydrofuran, trichloromethane, and combinations thereof. Suitable examples of non-polar solvents include, but are not limited to, alkane and substituted alkane solvents (including cycloalkanes), aromatic hydrocarbons, esters, ethers, combinations thereof, and the like. Specific non-polar solvents that may be employed, include, for example, benzene, butyl acetate, t-butyl methyl-ether, chlorobenzene, chloroform, chloromethane, cyclohexane, dichloromethane, dichloroethane, diethyl ether, ethyl acetate, diethylene glycol, fluorobenzene, heptane, hexane, isopropyl acetate, methyltetrahydrofuran, pentyl acetate, n-propyl acetate, tetrahydrofuran, toluene, and combinations thereof. Exemplary solvents include acetonitrile, chloroform, dichloromethane, N,N-dimethylacetamide, N,N-dimethylformamide, N-methyl-2-pyrrolidinone, ethyl acetate, ethanol, and methanol. In embodiments in which the amine source is a primary amine, the preferred solvent is acetonitrile. In embodiments in which the amine source is an ammonium salt, the preferred solvent is ethanol.

In general, the weight ratio of the solvent to the compound comprising Formula (I) will range from about 0.5:1 to about 100:1. In various embodiments, the weight ratio of the solvent to the compound comprising Formula (I) may range from 0.5:1 to about 5:1, from about 5:1 to about 25:1, or from about 25:1 to about 100:1. In preferred embodiments, the weight ratio of the solvent to the compound comprising Formula (I) may range from about 2:1 to about 10:1.

(v) Reaction Conditions

In general, the reaction will be conducted at a temperature that ranges from about 20° C. to about 100° C., or more preferably from about 20° C. to about 70° C. In various embodiments, the temperature of the reaction may be about room temperature (~23° C.), about 30° C., about 40° C., about 50° C., about 60° C., or about 70° C. The reaction typically is performed under ambient atmosphere and pressure.

Generally, the reaction is allowed to proceed for a sufficient period of time until the reaction is complete, as determined by any method known to one skilled in the art, such as chromatography (e.g., HPLC). The duration of the reaction may range from about 12 hours to more than 3 days. In some embodiments, the reaction may be allowed to proceed for 12 hours, 18 hours, 24 hours, 36 hours, 48 hours, 60 hours, 72 hours, or 84 hours. In this context, a "completed reaction" generally means that the reaction mixture contains a significantly diminished amount of the compound comprising Formula (I). Typically, the amount of the compound comprising Formula (I) remaining in the reaction mixture may be less than about 3%, and preferably less than about 1%.

(b) Intermediate Compounds

During step A of the process, the reductive amination of the compound comprising Formula (I) leads to the formation of two intermediate compounds comprising Formulas (IIa) or (IIb), as depicted in Reaction Scheme 1. The imine moiety of each is converted in situ to the 6-alpha-amino epimer, and extension of the reaction favors formation of the N17-formylated morphinan. As a consequence, an intermediate comprising Formula (III) is formed, as shown in Reaction Scheme 1. Additionally, the solvent of reaction mixture may be azeotropically dried, thereby further driving formation of the compound comprising Formula (III).

The compound comprising Formula (III) may precipitate out of the reaction mixture, and may be recovered from the reaction mixture using standard procedures. In other embodiments, the compound comprising Formula (III) may be isolated from the reaction mixture using standard procedures known to those of skill in the art.

(c) Step B of the Process

The process further comprises contacting the compound comprising Formula (III) with a proton acceptor, wherein the compound comprising Formula (IV) is formed. A variety of proton acceptors are suitable for use in this step of the process. In general, the proton acceptor will have a pKa greater than about 9. Suitable proton acceptors having this characteristic include ammonia, borate salts (such as, for example, $NaBO_3$), bicarbonate salts (such as, for example, $NaHCO_3$, $KHCO_3$, $LiCO_3$, and the like), carbonate salts (such as, for example, $Na_2CO_3$, $K_2CO_3$, $Li_2CO_3$, and the like), hydroxide salts (such as, for example, NaOH, KOH, and the like), organic bases (such as, for example, pyridine, methylamine, diethylamine, triethylamine, diisopropylethylamine, N-methylmorpholine, N,N-dimethylaminopyridine), and mixtures of any of the above. In preferred embodiments, the proton acceptor may be ammonia, ammonium hydroxide, potassium hydroxide, or sodium hydroxide. In an exemplary embodiment, the proton acceptor may be ammonia.

Typically, the amount of proton acceptor that is added to the reaction will be sufficient to adjust the pH of the reaction mixture to a value between 9 and 10. Preferably, the pH of the reaction mixture does not exceed 10. In some embodiments, the pH of the reaction mixture may range from about 9.0 to about 9.2, from about 9.2 to about 9.4, from about 9.4 to about 9.6, from about 9.6 to about 9.8, or from about 9.8 to about 10.0. In exemplary embodiments, the pH of the reaction mixture may range from about 9.3 to about 9.6. The proton acceptor may be may be added in small aliquots or dropwise to the reaction mixture until the desired the pH is reached.

The reaction mixture may further comprise a protic solvent. Suitable protic solvents are listed above in section (II)(a)(iv). In exemplary embodiments, the protic solvent may be water.

Typically, the reaction is allowed to proceed at room temperature for a sufficient period of time until the reaction is complete. Generally, the compound comprising Formula (IV) precipitates out of the reaction mixture. Accordingly, the reaction may be complete when no further precipitate is formed. Alternatively, the reaction may be determined complete by any known to those of skill in that, such as chromatography (e.g., HPLC). In this context, a "completed reaction" generally means that the reaction mixture contains a significantly diminished amount of the compound comprising Formula (III) and a significantly increased amount of the compound comprising Formula (IV) compared to the amounts of each present at the beginning of the reaction. Typically, the amount of the compound comprising Formula (III) remaining in the reaction mixture may be less than about 3%, and preferably less than about 1%.

The compound comprising Formula (IV) may be isolated from the reaction mixture using techniques known to those of skill in the art. Non-limiting examples of suitable techniques include precipitation, extraction, evaporation, chromatography, and crystallization.

The yield of the compound comprising Formula (IV) can and will vary. Typically, the yield of the compound comprising Formula (IV) will be at least about 60%. In one embodiment, the yield of the compound comprising Formula (IV) may range from about 60% to about 70%. In another embodiment, the yield of the compound comprising Formula (IV) may range from about 70% to about 80%. In a further embodiment, the yield of the compound comprising Formula (IV) may range from about 80% to about 90%. In still another embodiment, the yield of the compound comprising Formula (IV) may be greater than about 90%.

In embodiments in which the amine source is an ammonium salt, the final product further comprises an N-formyl-6-alpha-amino-N17-formyl morphinan comprising Formula (V):

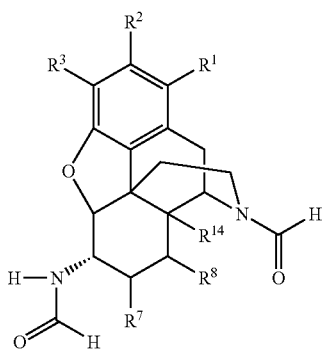

(V)

wherein R¹, R², R³, R⁷, R⁸, and R¹⁴ are as defined above in Reaction Scheme 1.

The compound comprising Formulas (IV) or (V) may be used as is or it may be converted to another compound using techniques familiar to those of skill in the art. The compound comprising Formulas (IV) or (V) may also be converted into a pharmaceutically acceptable salt. Pharmaceutically acceptable cations include metallic ions and organic ions. More preferred metallic ions include, but are not limited to, appropriate alkali metal salts, alkaline earth metal salts, and other physiologically acceptable metal ions. Exemplary ions include aluminum, calcium, lithium, magnesium, potassium, sodium, and zinc in their usual valences. Preferred organic ions include protonated tertiary amines and quaternary ammonium cations including, in part, trimethylamine, diethylamine, N,N'-dibenzylethylenediamine, chloroprocaine, choline, diethanolamine, ethylenediamine, meglumine (N methylglucamine) and procaine. Exemplary pharmaceutically acceptable acids include, without limitation, hydrochloric acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid, oxalacetic acid, fumaric acid, propionic acid, aspartic acid, glutamic acid, benzoic acid, and the like.

In general, the compound(s) prepared by the processes of the invention are enantiomerically pure in that the final product comprises less than about 5% of a 6-beta-amino epimer. In some embodiments, the final product may comprise less than about 2% of the 6-beta-amino epimer. In further embodiments, the final product may comprise less than about 1% of the 6-beta-amino epimer.

The compounds comprising any of Formulas (I), (IIa), (IIb), (III), (IV), or (V) may have a (−) or a (+) orientation with respect to the to the rotation of polarized light. More specifically, each chiral center of the morphinans may have an R or an S configuration. The compounds described herein may have at least four chiral centers, namely carbons C-5, C-9, C-13, and C-14. At each chiral center, the stereochemistry at the carbon atom is independently R or S. The configuration of C-5, C-9, C-13, and C-14, respectively, may be RRRR, RRRS, RRSR, RSRR, SRRR, RRSS, RSSR, SSRR, SRRS, SRSR, RSRS, RSSS, SRSS, SSRS, SSSR, or SSSS, provided that the C-15 and C-16 atoms are both on the alpha face of the molecule or both on the beta face of the molecule. The 6-alpha-amino group, i.e., {—}NHR⁶, may be R or S, depending on the identity (or priority) of R⁶.

In preferred embodiments, the compound produced by the process of the invention is a compound as diagrammed below or a pharmaceutically acceptable salt of the compound.

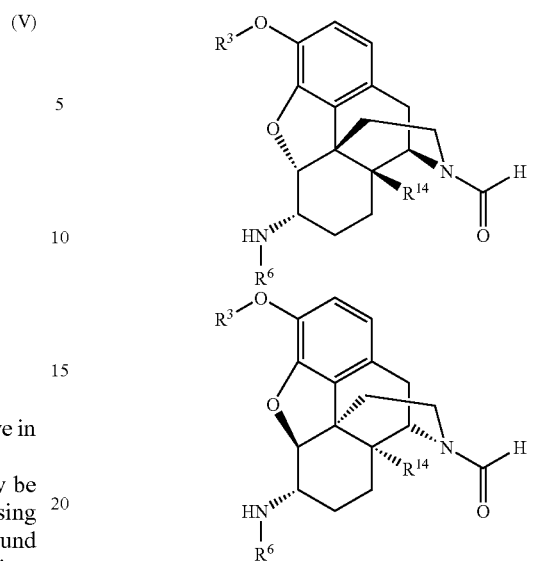

wherein:
R³ is selected from the group consisting of hydrogen, alkyl, and a protecting group;
R⁶ is selected from the group consisting of hydrogen, hydrocarbyl, and substituted hydrocarbyl; and
R¹⁴ is selected from the group consisting of hydrogen and hydroxy.

In preferred embodiments, R is methyl, cyclopropylmethyl, or allyl, and R³ is hydrogen or methyl.

(III) Compositions

A further aspect of the invention encompasses an epimerically pure composition comprising a compound of Formula (IV) and less than about 5% of a 6-beta amino epimer of the compound comprising Formula (IV):

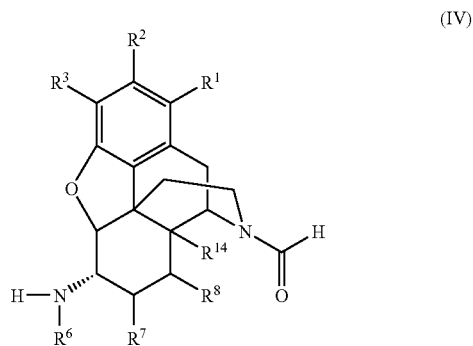

(IV)

wherein R¹, R², R³, R⁶, R⁷, R⁸, and R¹⁴ are as defined above in Reaction Scheme 1.

Moreover, the compounds of the composition may be pharmaceutically acceptable salts of the compound comprising Formula (IV), as detailed above in section (II)(c).

In one embodiment, the composition of the invention comprises less than about 2% of the 6-beta amino epimer. In another embodiment, the composition of the invention comprises less than about 1% of the 6-beta amino epimer. In a further embodiment, the composition of the invention comprises more than about 95% of the 6-alpha-amino epimer. In still another embodiment, the composition of the invention comprises more than about 98% of the 6-alpha-amino epimer. In a further embodiment, the composition of the invention comprises more than 99% of the 6-alpha-amino epimer.

The composition of the invention may be formulated for administration by a number of different means that will deliver a therapeutically effective dose. Such formulations may be administered orally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980).

DEFINITIONS

The compounds described herein have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "allyl," as used herein not only refers to compound containing the simple allyl group ($CH_2=CH-CH_2-$), but also to compounds that contain substituted allyl groups or allyl groups forming part of a ring system.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

As used herein, the term "6-amino" encompasses primary and secondary amine moieties conjugated to C-6 of a morphinan.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "protecting group" as used herein denotes a group capable of protecting an oxygen atom (and hence, forming a protected hydroxy), wherein the protecting group may be removed, subsequent to the reaction for which protection is employed, without disturbing the remainder of the molecule. Exemplary protecting groups include ethers (e.g., allyl, triphenylmethyl (trityl or Tr), p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl(TBDMS), t-butyldiphenylsilyl (TBDPS) and the like. A variety of protecting groups and the synthesis thereof may be found in "Protective Groups in Organic Synthesis" by T. W. Greene and P. G. M. Wuts, John Wiley & Sons, 1999.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples are included to demonstrate preferred embodiments of the invention. It should be appreciated by those of skill in the art that the techniques disclosed in the examples represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth is to be interpreted as illustrative and not in a limiting sense.

Example 1

Reductive Amination of (−)-Noroxymorphone with Benzylamine

The following reaction scheme depicts the preparation of 6-alpha-amino derivatives of (−)-noroxymorphone:

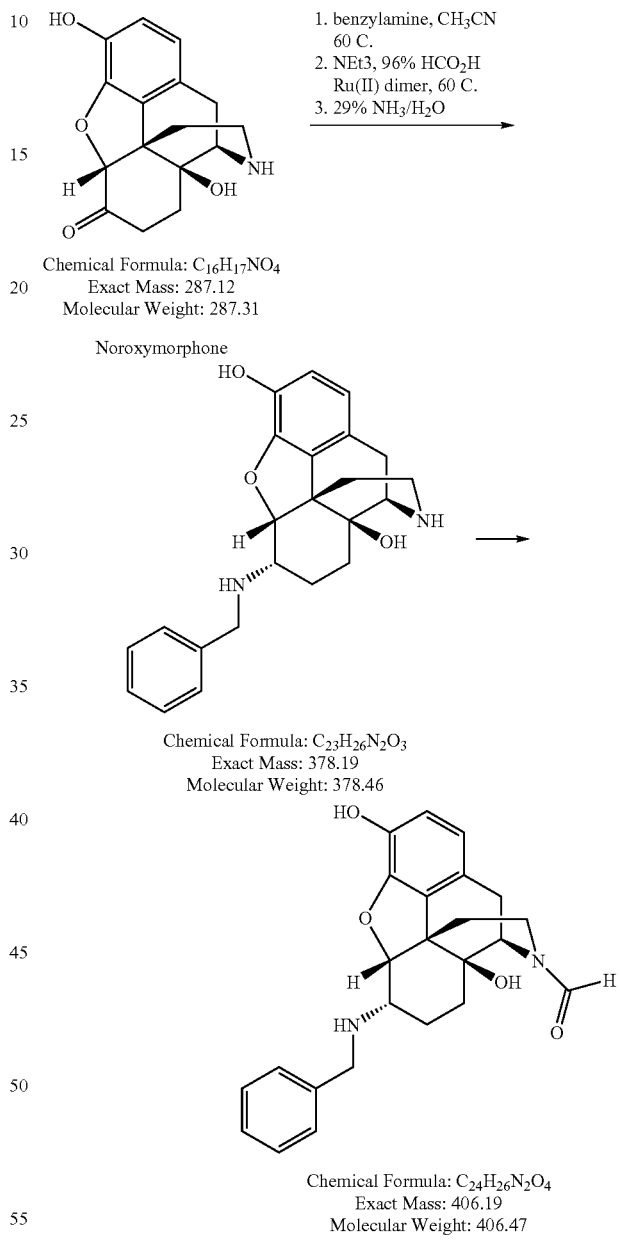

Reaction 1. Into a round bottom flask was added noroxymorphone (2.50 g, 0.009 moles), benzylamine (1.86 g, 0.017 moles, 1.83 mL), triethylamine (4.40 g, 0.044 moles, 6.06 mL), and acetonitrile (10 mL). To this solution was added >96% formic acid (5.01 g, 0.109 moles, 4.10 mL). The reaction temperature exothermed to 50° C. The reaction was stirred for 30 minutes until the temperature reached 25° C. Then, dichloro(p-cymene)Ru(II) dimer (27 mg) was added and the reaction was warmed to 60° C. for 18 h. LC indicated the noroxymorphone was consumed and two products were present, the N-formyl and the N—H compound. The reaction mixture was cooled to room temperature, and then evaporated to an oil. The residue was dissolved in acetonitrile (5 mL) and 29% $NH_3/H_2O$ was added dropwise until the pH of the mixture was 9.4. After stirring for 1 h, the aqueous mixture was extracted with 10% isopropanol/chloroform (3×25 mL). The extracts were combined, dried over anhydrous $MgSO_4$, filtered, and evaporated to dryness. The N-formyl compound (2.30 g, 65% yield) was isolated by gravity column chromatography (Silica Gel G60, 15 g) eluting with 5% MeOH/$CHCl_3$. The desired fractions were combined, the solvent was evaporated, and the resultant residue was placed under vacuum (24 h, room temperature).

Reaction 2. Into a round bottom flask was added (−)-noroxymorphone (2.50 g, 0.009 moles), benzylamine (1.86 g, 0.017 moles, 1.83 mL), triethylamine (4.40 g, 0.044 moles, 6.06 mL), and acetonitrile (10 mL). To this solution was added >96% formic acid (5.01 g, 0.109 moles, 4.10 mL). The reaction exothermed to 50° C. The reaction was stirred for 30 minutes until the temperature reached 25° C. Then, dichloro(p-cymene)Ru(II) dimer (27 mg) was added and the reaction was stirred at room temperature for 30 h. LC indicated the noroxymorphone was consumed and two products were present, the N-formyl and the N—H compound. Then, the reaction was heated to 60° C. for 48 h. HPLC indicated predominately the N-formyl and some N—H. The reaction was cooled to room temperature, and then the reaction mixture was evaporated to an oil. The residue was dissolved in acetonitrile (5 mL) and 29% $NH_3/H_2O$ was added drop wise to pH 9.4. After stirring for 1 h, distilled water (5 mL) was added then the mixture was extracted with 10% isopropanol/chloroform (3×25 mL). The extracts were combined, dried over anhydrous $MgSO_4$, filtered, and evaporated to dryness. The N-formyl compound (2.30 g, 65% yield) was isolated by gravity column chromatography (Silica Gel G60, 20 g) eluting with 5% MeOH/$CHCl_3$, combining the desired fractions, evaporating, then placing the residue under vacuum (24 h, room temperature).

Example 2

Reductive Amination of (+)-Noroxymorphone with Benzylamine

A 6-alpha amino derivative of (+)-noroxymorphone was prepared according to the following reaction scheme:

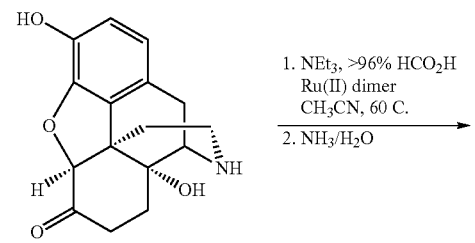

Chemical Formula: $C_{16}H_{17}NO_4$
Exact Mass: 287.12
Molecular Weight: 287.31

(+)-Noroxymorphone

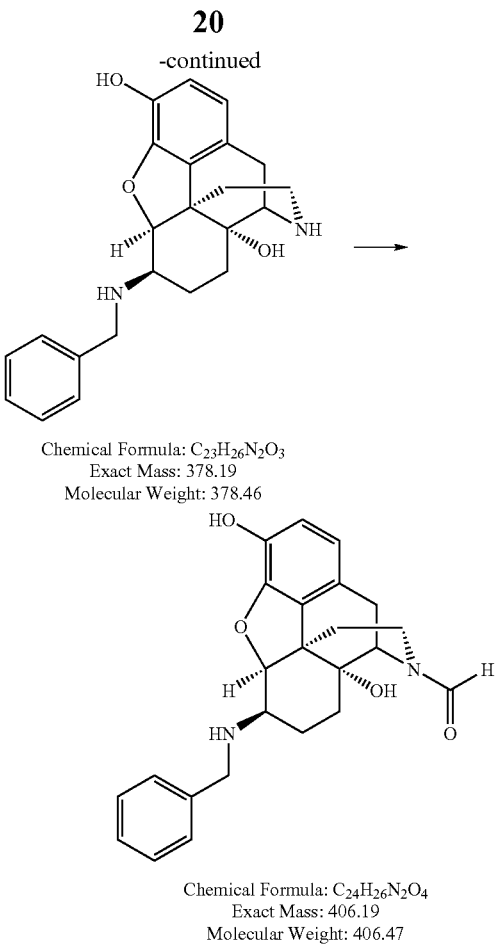

Chemical Formula: $C_{23}H_{26}N_2O_3$
Exact Mass: 378.19
Molecular Weight: 378.46

Chemical Formula: $C_{24}H_{26}N_2O_4$
Exact Mass: 406.19
Molecular Weight: 406.47

Reaction 1. Into a round bottom flask was charged (+)-noroxymorphone (0.50 g, 1.74 mmoles), acetonitrile (20.0 mL), and then benzylamine (0.37 g, 3.45 mmoles). This mixture was stirred at room temperature for 5 minutes, then triethylamine (0.88 g, 8.7 mmoles, 1.21 mL) was added. Next, >96% formic acid (1.0 g, 21.72 mmoles, 0.82 mL) was added dropwise. The temperature exothermed to 45° C. After the addition of formic acid was complete, dichloro(p-cymene) Ru(II) dimer (5 mg, 0.008 mmole) was added. The reaction mixture was stirred at 60° C. for 48 h. Then, an additional amount of >96% formic acid (0.61 g, 13.25 mmol, 0.5 mL) was added. After stirring for an additional 24 h at 60° C., the reaction was determined to by complete by HPLC. The reaction mixture was evaporated under reduced pressure to a thick oil. To this oil was added distilled water (10 mL) then the pH of this solution was adjusted to 9.6 using 29% $NH_3/H_2O$. The aqueous layer was extracted with $CHCL_3$ (3×25 mL), the extracts were combined, dried over anhydrous $MgSO_4$, filtered, and evaporated to an oil. The product (600 mg, 1.47 mmoles, 85% yield) was isolated by column chromatography (Silica Gel G60, 70 to 230 mesh ASTM) using a gradient elution from 2.5% MeOH/$CHCl_3$ to 5.0% MeOH/$CHCl_3$. The appropriate fractions were combined, the solvent was evaporated, and the resultant oil was placing under vacuum for 24 h at room temperature producing an off white foam.

Reaction 2. Into a round bottom flask was added (+)-noroxymorphone (0.48 g, 0.002 moles), benzylamine (0.27 g, 0.003 moles, 0.27 mL), triethylamine (0.84 g, 0.008 moles, 1.16 mL), and acetonitrile (5.0 mL). After cooling the reaction to 5° C. (ice/water), >96% formic acid (0.96 g, 0.021 moles, 0.79 mL) was added drop wise. The reaction temperature exothermed to 50° C. The reaction was stirred for 30 minutes until the temperature reached 25° C. Then, dichloro (p-cymene)Ru(II) dimer (5 mg) followed by acetonitrile (5.0 mL) was added and the reaction was stirred at room temperature for 48 h. LC indicated the noroxymorphone was consumed and two products were present, the N-formyl and the N—H compound. Then, the reaction was heated to 65° C. for 48 h. LC indicated predominately the N-formyl and some N—H. The reaction was cooled to room temperature, transferred into a round bottom flask (rinsing the reaction flask with 5.0 mL acetonitrile), and then the reaction mixture was evaporated to an oil. The residue was dissolved in distilled water (10 mL) and 29% $NH_3/H_2O$ was added drop wise to pH 9.8. After stirring for 1 h, the mixture was extracted with 10% isopropanol/chloroform (3×25 mL). The organic extracts were combined, dried over anhydrous $MgSO_4$, filtered, and evaporated to dryness. The remaining aqueous solution was evaporated to dryness. After combining the residues from the organic extracts and aqueous solution, the N-formyl compound (0.39 g, 57% yield) was isolated by gravity column chromatography (Silica Gel G60, 15 g) using a gradient elution from $CHCl_3$ to 5% $MeOH/CHCl_3$, combining the desired fractions, evaporating, then placing the residue under vacuum (24 h, room temperature).

What is claimed is:

1. A process for preparing a 6-alpha-amino-N17-formyl morphinan, the process comprising contacting a 6-keto normorphinan with an amine source, a hydrogen donor comprising a formate ion, a transition metal catalyst, and a proton acceptor to form the 6-alpha-amino-N17-formyl morphinan.

2. The process of claim 1, wherein the 6-keto normorphinan is selected from a group consisting of norhydrocodone, norhydromorphone, noroxycodone, and noroxymorphone; the amine source is chosen selected from a group consisting of a primary amine and an ammonium salt; the hydrogen donor comprising a formate ion is selected from a group consisting of formic acid, a salt of formic acid, and a mixture of formic acid and an organic base; the transition metal catalyst comprises ruthenium, rhodium, or iridium; and the proton acceptor has a pKa of great than about 9.

3. The process of claim 1, wherein at least one intermediate compound comprising a 6-imine moiety is produced during the process.

4. The process of claim 1, wherein the 6-alpha-amino-N17-formyl morphinan comprises no more than about 2% of a 6-beta-amino epimer.

5. A process for preparing a compound of Formula (IV):

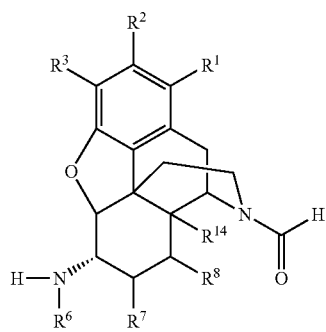

the process comprising:
reducing a compound of Formula (I) in the presence of an amine source ($R^6NH_2$), a hydrogen donor comprising a formate ion, a transition metal catalyst, and a proton acceptor to form the compound of Formula (IV), the compound of Formula (I) having the structure:

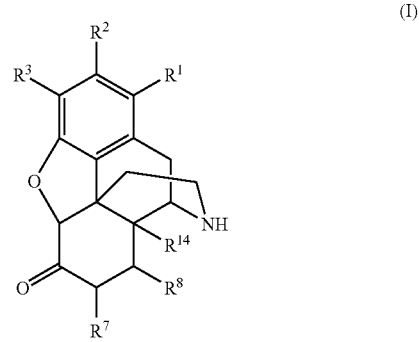

wherein:
$R^1$ and $R^2$ are independently selected from a group consisting of hydrogen, hydrocarbyl, substituted hydrocarbyl, halogen, and {—}$OR^{15}$;
$R^3$, $R^7$, and $R^8$ are independently selected from a group consisting of hydrogen, hydrocarbyl, substituted hydrocarbyl, and {—}$OR^{15}$;
$R^6$ is selected from a group consisting of hydrogen, hydrocarbyl and substituted hydrocarbyl;
$R^{14}$ is selected from a group consisting of hydrogen and {—}$OR^{15}$; and
$R^{15}$ is selected from a group consisting of hydrogen, hydrocarbyl, substituted hydrocarbyl, and a hydroxy protecting group.

6. The process of claim 5, wherein $R^1$, $R^2$, $R^7$, and $R^8$ are hydrogen; $R^3$ is selected from a group consisting of alkoxy, hydroxy, and protected hydroxy; $R^{14}$ is hydrogen or hydroxyl; $R^6$ is selected from a group consisting of hydrogen, alkyl, substituted alkyl, alkenyl, substituted alkenyl, and aryl; the hydrogen donor comprising a formate ion is selected from a group consisting of formic acid, a salt of formic acid, and a mixture of formic acid and an organic base; $R^6$ is selected from a group consisting of alkyl, substituted alkyl, alkenyl, substituted alkenyl, and aryl, and the amine source is a primary amine; the molar ratio of the compound of Formula (I) to the primary amine to the hydrogen donor is from about 1:1:1 to about 1:5:20; the transition metal catalyst comprises ruthenium, rhodium, or iridium; the molar ratio of the compound of Formula (I) to the transition metal catalyst is about 1:0.0001 to about 1:0.01; the reaction of the compound of Formula (I), the amine source, the transition metal catalyst, and the hydrogen donor occurs in the presence of a solvent selected from a group consisting of an aprotic solvent, a protic solvent, a non-polar solvent, and combinations thereof and occurs at a temperature from about 20° C. to about 100° C.; the proton acceptor has a pKa of greater than about 9 and the proton acceptor is selected from a group consisting of ammonia, ammonium hydroxide, potassium hydroxide, and sodium hydroxide.

7. The process of claim 5, wherein $R^6$ is hydrogen and the amine source is an ammonium salt.

8. The process of claim 7, wherein the molar ratio of the compound of Formula (I) to the ammonium salt to the hydrogen donor is from about 1:2:1 to about 1:20:20.

9. The process of claim 5, wherein the hydrogen donor comprises formic acid and triethylamine.

10. The process of claim 9, wherein the molar ratio of the compound of Formula (I) to triethylamine is from about 1:1 to about 1:10.

11. The process of claim 5, wherein the transition metal catalyst is selected from a group consisting of dichloro(arene) Ru(II) dimer, dichloro(pentamethylcyclopentadienyl)Rh(II) dimer, BINAP-Ru(II) diacetate, BINAP-Ru(II) dichloride, BINAP-Ru(II) dibromide, BINAP-Ru(II) diiodide, [RuCl((R or S)BINAP)($C_6H_6$)]Cl, dichloro(pentamethylcyclopentadieny)iridium(III) dimer, Ru(III) chloride, $RuCl_3$ hydrate, Ru(III) acetylacetonate, tetraalkylammonium $RuCl_4$, and pyridinium $RuCl_4$.

12. The process of claim 5, wherein the transition metal catalyst is a Noyori catalyst.

13. The process of claim 5, wherein two first intermediates of Formula (IIa) and Formula (IIb) are formed after the compound of Formula (I) is contacted with the amine source, the hydrogen source, and the transition metal catalyst; and the first intermediates are converted in situ to a second intermediate of Formula (III):

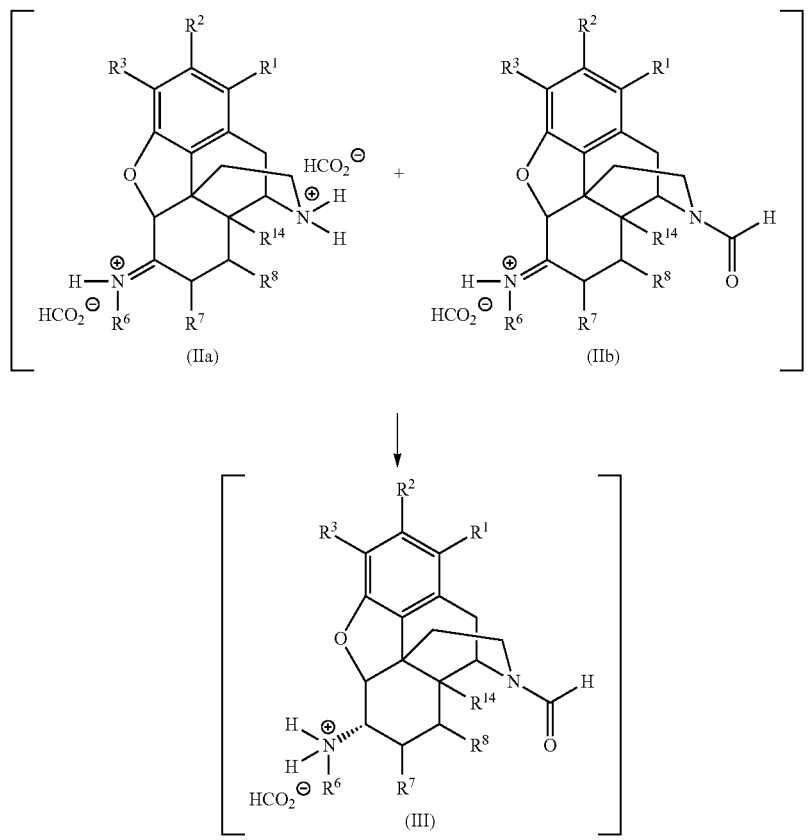

wherein:
$R^1$ and $R^2$ are independently selected from a group consisting of hydrogen, hydrocarbyl, substituted hydrocarbyl, halogen, and $\{-\}OR^{15}$;
$R^3$, $R^7$, and $R^8$ are independently selected from a group consisting of hydrogen, hydrocarbyl, substituted hydrocarbyl, and $\{-\}OR^{15}$;

$R^6$ is selected from a group consisting of hydrogen, hydrocarbyl and substituted hydrocarbyl;
$R^{14}$ is selected from a group consisting of hydrogen and $\{-\}OR^{15}$; and
$R^{15}$ is selected from a group consisting of hydrogen, hydrocarbyl, substituted hydrocarbyl, and a hydroxy protecting group.

14. The process of claim 5, wherein the compound of Formula (IV) has the structure of Formula (V):

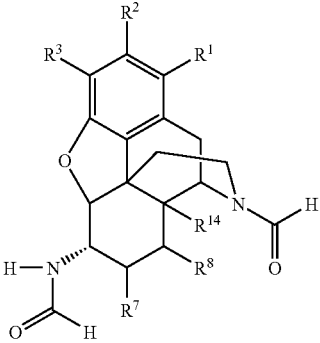

wherein:
$R^1$ and $R^2$ are independently selected from a group consisting of hydrogen, hydrocarbyl, substituted hydrocarbyl, halogen, and $\{-\}OR^{15}$;
$R^3$, $R^7$, and $R^8$ are independently selected from a group consisting of hydrogen, hydrocarbyl, substituted hydrocarbyl, and $\{-\}OR^{15}$;

$R^{14}$ is selected from a group consisting of hydrogen and {—}$OR^{15}$; and $R^{15}$ is selected from a group consisting of hydrogen, hydrocarbyl, substituted hydrocarbyl, and a hydroxy protecting group.

15. The process of claim 5, wherein the amine source is a primary amine; the molar ratio of the compound of Formula (I) to the primary amine is about 1:2; the hydrogen donor comprises formic acid and triethylamine; the molar ratio of the compound of Formula (I) to formic acid to triethylamine is about 1:12:3; the transition metal catalyst is dichloro(p-cymene)Ru(II) dimer; the molar ratio of the compound of Formula (I) to the Ru(II) dimer is from about 1:0.001 to 1:0.01; reaction with the primary amine, Ru(II) dimer, and formic acid/triethylamine occurs in the presence of acetonitrile and at a temperature from about 20° C. to about 70° C.; the proton acceptor is ammonia; and reaction with the proton acceptor occurs in a protic solvent system comprising water, at a pH of about 9.5, and at room temperature.

16. The process of claim 5, wherein the amine source is ammonium acetate; the molar ratio of the compound of Formula (I) to ammonium acetate is about 1:12; the hydrogen donor comprises formic acid and triethylamine; the molar ratio of the compound of Formula (I) to formic acid to triethylamine is about 1:12:5; the transition metal catalyst is dichloro(p-cymene)Ru(II) dimer; the molar ratio of the compound of Formula (I) to the Ru(II) dimer is from about 1:0.001 to 1:0.01; reaction of the ammonium acetate, the Ru(II) dimer, and the formic acid/triethylamine occurs in the presence of ethanol and at a temperature from about 20° C. to about 70° C.; the proton acceptor is ammonia; and reaction with the proton acceptor occurs in a protic solvent system comprising water, at a pH of about 9.5, and at room temperature.

17. The process of claim 5, wherein the optical activity of the compounds of Formulas (I) or (IV) is (−) or (+), the configuration of C-5, C-13, C-14, and C 9, respectively, is chosen from RRRR, RRRS, RRSR, RSRR, SRRR, RRSS, RSSR, SSRR, SRRS, SRSR, RSRS, RSSS, SRSS, SSRS, SSSR, and SSSS, provided that C-15 and C-16 are both either on the alpha face or the beta face of the molecule; and the compound of Formula (IV) comprises less than 2% of a 6-beta-amino epimer.

* * * * *